US012642556B2

(12) United States Patent
Ding et al.

(10) Patent No.: US 12,642,556 B2
(45) Date of Patent: Jun. 2, 2026

(54) TROCAR FOR CLEANING MEDICAL DEVICES THEREIN

(71) Applicant: Covidien LP, Mansfield, MA (US)

(72) Inventors: Weijiang Ding, Shanghai (CN); Syed Sarfraz Ahamed, Shanghai (CN); Kai Huang, Shanghai (CN); Kaizhi Zhang, Shanghai (CN)

(73) Assignee: Covidien LP, Mansfield, MA (US)

( * ) Notice: Subject to any disclaimer, the term of this patent is extended or adjusted under 35 U.S.C. 154(b) by 465 days.

(21) Appl. No.: 17/912,561

(22) PCT Filed: Mar. 19, 2020

(86) PCT No.: PCT/CN2020/080152
§ 371 (c)(1),
(2) Date: Sep. 19, 2022

(87) PCT Pub. No.: WO2021/184288
PCT Pub. Date: Sep. 23, 2021

(65) Prior Publication Data
US 2023/0172632 A1 Jun. 8, 2023

(51) Int. Cl.
*A61B 17/34* (2006.01)
*A61B 1/12* (2006.01)
*A61B 17/00* (2006.01)

(52) U.S. Cl.
CPC .......... *A61B 17/3423* (2013.01); *A61B 1/126* (2013.01); *A61B 2017/00566* (2013.01);
(Continued)

(58) Field of Classification Search
CPC ............ A61B 1/00135; A61B 1/00142; A61B 1/00154; A61B 1/015; A61B 1/126;
(Continued)

(56) References Cited

U.S. PATENT DOCUMENTS

| | | | |
|---|---|---|---|
| 5,972,020 A | 10/1999 | Carpentier et al. | |
| 9,039,604 B2 * | 5/2015 | Yoshida ............. | A61B 17/3474 604/266 |

(Continued)

FOREIGN PATENT DOCUMENTS

| | | | |
|---|---|---|---|
| AU | 2007219275 A1 † | 4/2008 | |
| CN | 101686840 A | 3/2010 | |

(Continued)

OTHER PUBLICATIONS

European extended search report issued in corresponding European application EP4120934A1, mailed Oct. 19, 2023.
(Continued)

*Primary Examiner* — Ryan N Henderson
(74) *Attorney, Agent, or Firm* — Dymera IP, LLC

(57) ABSTRACT

A trocar (10) is provided which permits cleaning of a medical device herein. In aspects, the trocar (10) has a seal (50) at a distal portion of the trocar (10). In use, a medical device, such as a laparoscope (200), passes through the seal (50) at the distal portion of the trocar (10). To clean a lens (210) at the end of the laparoscope (200), a vacuum is applied to the interior of the trocar (10), the laparoscope (200) is partially withdrawn so that it is proximal to the seal (50), and liquids and/or gases are introduced into the trocar (10) to clean the lens (210) while the laparoscope (200) remains within the trocar (10).

18 Claims, 6 Drawing Sheets

(52) U.S. Cl.
CPC .................. *A61B 2017/3419* (2013.01); *A61B 2017/3437* (2013.01); *A61B 2217/005* (2013.01)

(58) Field of Classification Search
CPC ..... A61B 1/127; A61B 1/00009; A61B 1/313; A61B 1/3132; A61B 1/12; A61B 17/3423; A61B 2017/3419; A61B 2017/3437; A61B 2017/00566
See application file for complete search history.

(56) References Cited

U.S. PATENT DOCUMENTS

| | | | | |
|---|---|---|---|---|
| 9,078,694 | B2 * | 7/2015 | Hartoumbekis | ....... A61B 1/126 |
| 11,583,176 | B2 * | 2/2023 | Aluru | ..................... A61B 17/34 |
| 11,751,759 | B2 * | 9/2023 | Burt | ........................ A61B 17/34 600/117 |
| 11,805,968 | B2 * | 11/2023 | Aluru | ................. A61B 17/3417 |
| 12,150,625 | B2 * | 11/2024 | Aluru | ..................... A61B 1/126 |
| 2007/0282253 | A1 * | 12/2007 | Sasaki | ..................... A61B 1/313 604/93.01 |
| 2008/0045859 | A1 * | 2/2008 | Fritsch | ................. A61B 18/148 600/567 |
| 2008/0081948 | A1 * | 4/2008 | Weisenburgh | ......... A61B 1/126 600/157 |
| 2008/0255424 | A1 * | 10/2008 | Durgin | ............... A61B 10/0283 600/156 |
| 2009/0005799 | A1 † | 1/2009 | Franer | |
| 2009/0234193 | A1 * | 9/2009 | Weisenburgh, II | .......................... A61B 1/00068 600/157 |
| 2009/0299137 | A1 * | 12/2009 | Gal | ........................ A61B 1/128 600/116 |
| 2010/0010310 | A1 * | 1/2010 | Weisenburgh, II | .. A61B 1/3132 600/156 |
| 2013/0041230 | A1 * | 2/2013 | Hartoumbekis | ... A61B 17/3421 600/205 |
| 2013/0053643 | A1 * | 2/2013 | Yoshida | ................. A61B 1/126 600/114 |
| 2015/0190041 | A1 * | 7/2015 | Suehara | ................. A61B 1/127 600/109 |
| 2018/0014908 | A1 * | 1/2018 | Katz | .................. A61B 1/00135 |
| 2018/0344427 | A1 * | 12/2018 | Rosenbaum | ........... A61B 90/70 |
| 2018/0360490 | A1 | 12/2018 | Rosenbaum et al. | |
| 2019/0125176 | A1 * | 5/2019 | Burt | ................... G02B 23/2476 |
| 2021/0127963 | A1 * | 5/2021 | Aluru | ................. A61B 17/3421 |
| 2021/0127964 | A1 * | 5/2021 | Aluru | ..................... A61B 17/34 |
| 2021/0236749 | A1 * | 8/2021 | Kokhanenko | ...... A61B 17/3421 |
| 2021/0322684 | A1 * | 10/2021 | Fischer | ............... A61M 13/003 |
| 2022/0175237 | A1 * | 6/2022 | De Abreu | .......... A61B 1/00135 |
| 2022/0192480 | A1 * | 6/2022 | Burt | ................... A61B 1/00006 |
| 2023/0165452 | A1 * | 6/2023 | Ding | .................. A61B 1/00135 600/114 |
| 2023/0414085 | A1 * | 12/2023 | Aluru | ................. A61B 17/3417 |
| 2024/0293018 | A1 * | 9/2024 | Aluru | ........................ A61L 2/16 |

FOREIGN PATENT DOCUMENTS

| | | | |
|---|---|---|---|
| CN | 104248464 | A | 12/2014 |
| CN | 107072521 | A | 8/2017 |
| CN | 107647905 | A † | 2/2018 |
| CN | 109124733 | A | 1/2019 |
| DE | 19523685 | A1 | 1/1997 |
| EP | 2111808 | A2 | 10/2009 |
| WO | 2013012367 | A1 | 1/2013 |

OTHER PUBLICATIONS

International Search Report issued in corresponding application PCT/CN2020/080152 mailed Dec. 1, 2020 (7 pages).
Written Opinion of the International Searching Authority issued in corresponding application PCT/CN2020/080152 mailed Dec. 1, 2020 (5 pages).
Chinese First Office Action dated Nov. 12, 2024, issued in corresponding Chinese Application No. 202080098549.2, 9pgs.
CN Office Action, 202080098377.9, Sep. 30, 2024, 7 pgs.
"Communication pursuant to Article 94(3) EPC", European Application No. 20 926 301.1-1113, Feb. 6, 2025, 6pgs.
Chinese Second Office Action mailed Jul. 28, 2025, Chinese Application No. 202080098549.2, 8pgs.
Chinese Second Office Action mailed Jul. 28, 2024, Chinese Application No. 202080098549.2, 8pgs.
European Examination Report mailed Aug. 1, 2025, European Application No. 20 926 301.1-1113, 6pgs.
European Patent Office Examination Report, communication pursuant to Article 94(3) EPC, from counterpart European Application No. 20 926 301.1-1113, dated Mar. 11, 2026, pp. 7.

* cited by examiner
† cited by third party

TROCAR FOR CLEANING MEDICAL DEVICES THEREIN

CROSS-REFERENCE TO RELATED APPLICATIONS

This application is a U.S. National Stage Application filed under 35 U.S.C. § 371(a) of International Patent Application No. PCT/CN2020/080152, filed Mar. 19, 2020.

TECHNICAL FIELD

The disclosure relates to a surgical apparatus for use in minimally invasive surgical procedures, such as endoscopic and/or laparoscopic procedures and, more particularly, to a trocar that includes mechanisms for cleaning devices therein.

BACKGROUND

Minimally invasive surgery, such as endoscopic surgery, reduces the invasiveness of surgical procedures. Endoscopic surgery involves surgery through body walls, for example, viewing and/or operating on the ovaries, uterus, gall bladder, bowels, kidneys, appendix, etc. There are many common endoscopic surgical procedures, including arthroscopy, laparoscopy, gastroentroscopy and laryngobronchoscopy, just to name a few. In these procedures, trocars are utilized for creating incisions through which the endoscopic surgery is performed. Trocar tubes or cannula devices are extended into and left in place in the abdominal wall to provide access for endoscopic surgical tools. A camera or laparoscope is inserted through a trocar tube to permit the visual inspection and magnification of the body cavity. The surgeon can then perform diagnostic and/or therapeutic procedures at the surgical site with the aid of specialized instrumentation, such as forceps, graspers, cutters, applicators, and the like, which are designed to fit through additional cannulas.

In use, a lens of a laparoscope can become covered by condensation, tissue, blood, other body fluids, etc. Keeping the lens of a laparoscope clean during a procedure is thus difficult, and the time needed to clean the laparoscope during the procedure can increase both the overall time of the procedure and the amount of time a patient needs to remain under anesthesia, both of which can lead to increased risk of infection and increased recovery time.

SUMMARY

Trocars for use in minimally invasive surgery are provided. In aspects, a trocar of the disclosure includes an elongate body defining a lumen, the elongate body having a proximal portion and a distal portion, a seal assembly at the proximal portion of the elongate body, an inlet port at the proximal portion of the elongate body, and a vacuum port at the proximal portion of the elongate body. The trocar also has an inlet tube affixed to the inlet port, the inlet tube terminating at an entry opening within the distal portion of the elongate body, and an outlet tube affixed to the vacuum port, the outlet tube terminating at an exit opening within the distal portion of the elongate body. The trocar has a vacuum seal at the distal portion of the elongate body.

In some aspects, the vacuum seal is formed of multiple leaflets. In aspects the vacuum seal is distal to the entry opening of the inlet tube and the exit opening of the vacuum tube.

Kits including the disclosed trocars are also provided. In aspects, the kit includes a cannula, a laparoscope, and the disclosed trocar. The trocar fits within a lumen of the cannula. The laparoscope fits within a lumen of the trocar.

Methods for using the disclosed trocars/kits to clean a medical device during a surgical procedure are also provided. A method for cleaning a medical device includes introducing the disclosed trocar into a patient's body, and introducing a laparoscope through the trocar into the patient's body. When the end of the laparoscope, including the lens, needs to be cleaned, a vacuum is drawn on the vacuum port, and the laparoscope is partially withdrawn so that the lens at a distal portion of the laparoscope is proximal the vacuum seal within a lumen of the trocar. The method includes introducing a liquid through the inlet port, the inlet tube, and entry opening into the lumen of the trocar at a distal portion of the elongate body, where it contacts the lens of the laparoscope, and then removing the liquid out the exit opening, the vacuum tube and the vacuum port.

The liquid used to clean the medical device includes water, saline, and combinations thereof.

Drawing the vacuum and partially withdrawing the laparoscope causes the vacuum seal in the trocar to close.

In aspects, the method further includes introducing a gas through the inlet port, the inlet tube, and entry opening into the lumen of the trocar at the distal portion of the elongate body, where it contacts the lens of the laparoscope, and then removing the gas out the exit opening, the vacuum tube and the vacuum port.

In some aspects, the gas is introduced after the liquid. Suitable gases include air, carbon dioxide, or combinations thereof.

Once cleaned, the method includes distally passing the laparoscope through the vacuum seal and back into the patient's body for further use.

BRIEF DESCRIPTION OF THE DRAWINGS

Various aspects of the disclosed trocar are described herein below with reference to the drawings, wherein.

DETAILED DESCRIPTION

Figure 1:
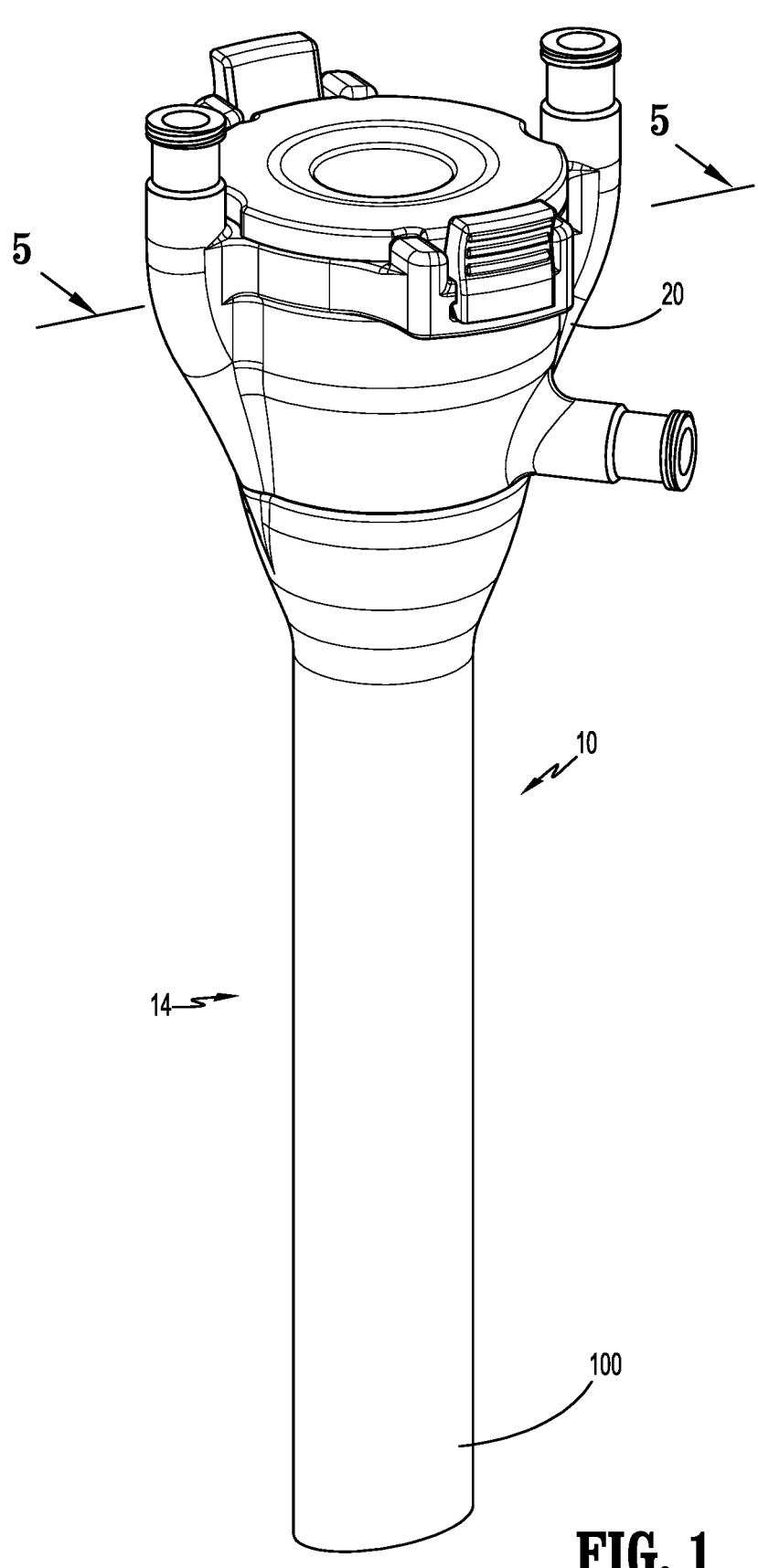
FIG. 1 is a side perspective view of a trocar of the disclosure placed within a cannula.

The disclosed trocars are described in detail with reference to the drawings, in which like reference numerals designate identical or corresponding elements in each of the several views. As used herein the term "distal" refers to that portion of the trocar, or component thereof, farther from the user, while the term "proximal" refers to that portion of the trocar, or component thereof, closer to the user.

Figure 2:
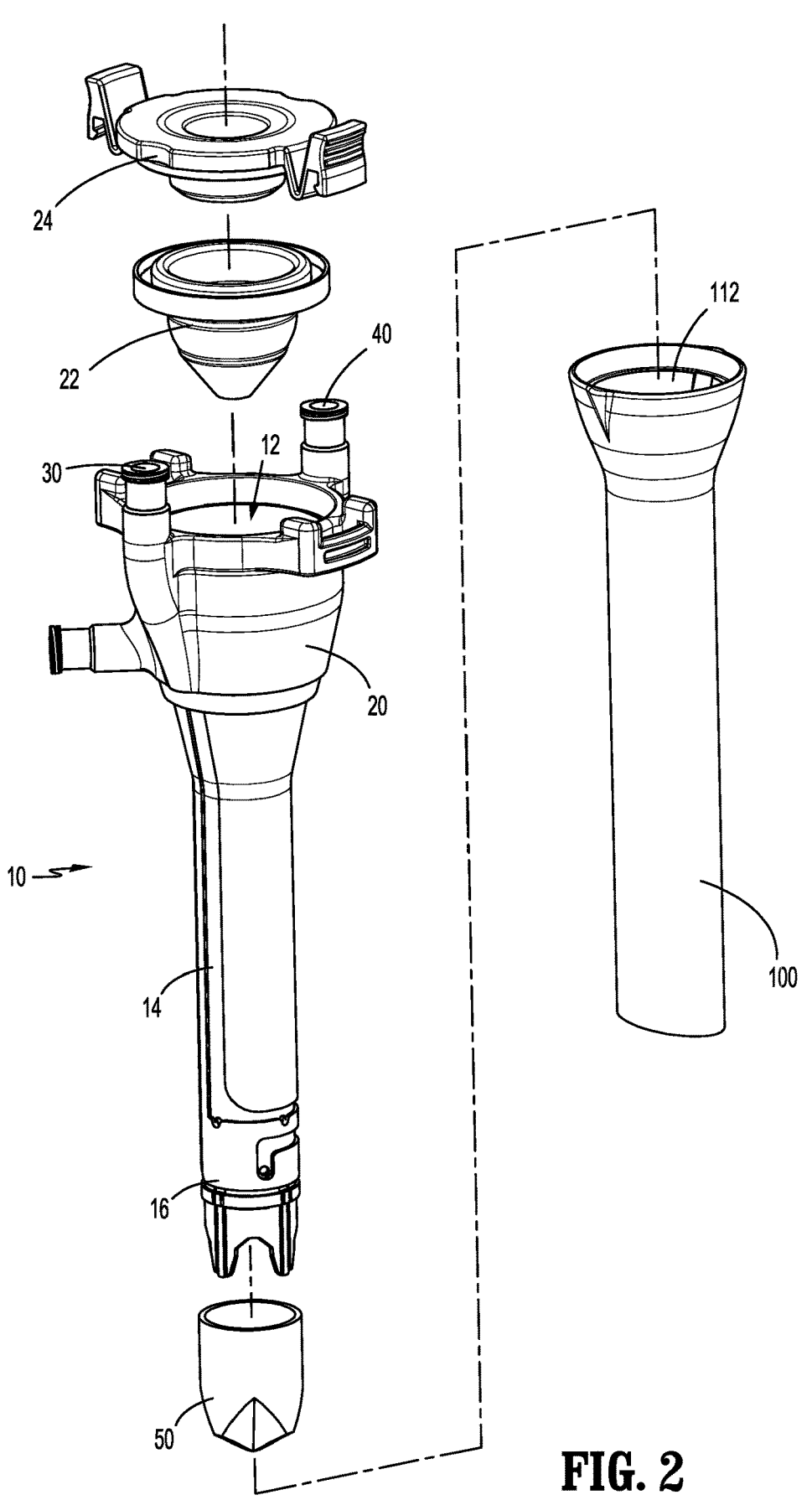
FIG. 2 is a side view of the trocar and the cannula of FIG. 1 in a disassembled state.

FIGS. 1-4 depict a trocar in accordance with an aspect of the disclosure. As shown in FIG. 1, trocar 10 is for use with a cannula 100. As shown in FIG. 2, cannula 100 has a lumen 112 through which trocar 10 may pass. Trocar 10 has a lumen 12 through which a medical device may pass. The trocar 10 includes a seal assembly 20, an elongate body 14, a distal portion 16, and a proximal portion 18. As shown in FIG. 2, the seal assembly 20 includes a seal 22 for placement therein and a securing collar 24 for maintaining the seal 22 within the seal assembly 20. The trocar 10 also has an inlet port 30 and a vacuum port 40. A liquid, such as water or saline, and/or a gas, such as air or carbon dioxide, may be introduced into the trocar 10 through the inlet port 30, and the liquid and/or gas may be removed from the trocar 10 through the vacuum port 40.

Figures 3, 4:
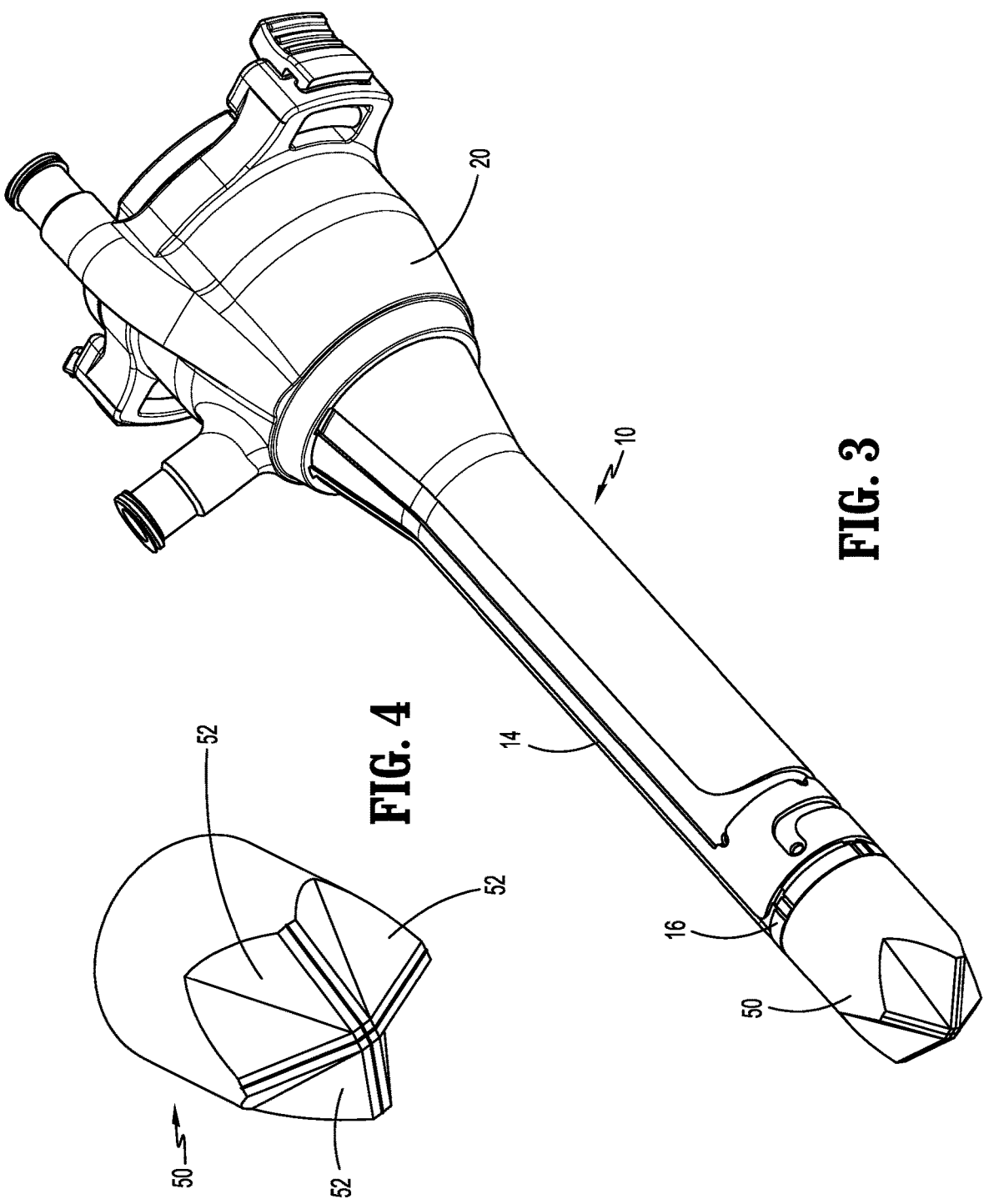
FIG. 3 is a side perspective view of the trocar of the disclosure.
FIG. 4 is a side perspective view of a seal of the trocar shown in FIG. 1 located at a distal portion of the trocar of the disclosure.

The trocar 10 also has a vacuum seal 50 at the distal portion 16 of the trocar 10 (FIGS. 3-4). As shown in greater detail in FIG. 4, the vacuum seal 50 may be formed of multiple leaflets 52 which permit passage of a medical device therethrough, but the multiple leaflets 52 will close the vacuum seal 50 when a medical device is removed therefrom. Moreover, a vacuum drawn on the vacuum port 40, will maintain the vacuum seal 50 in a closed position.

Figure 5:
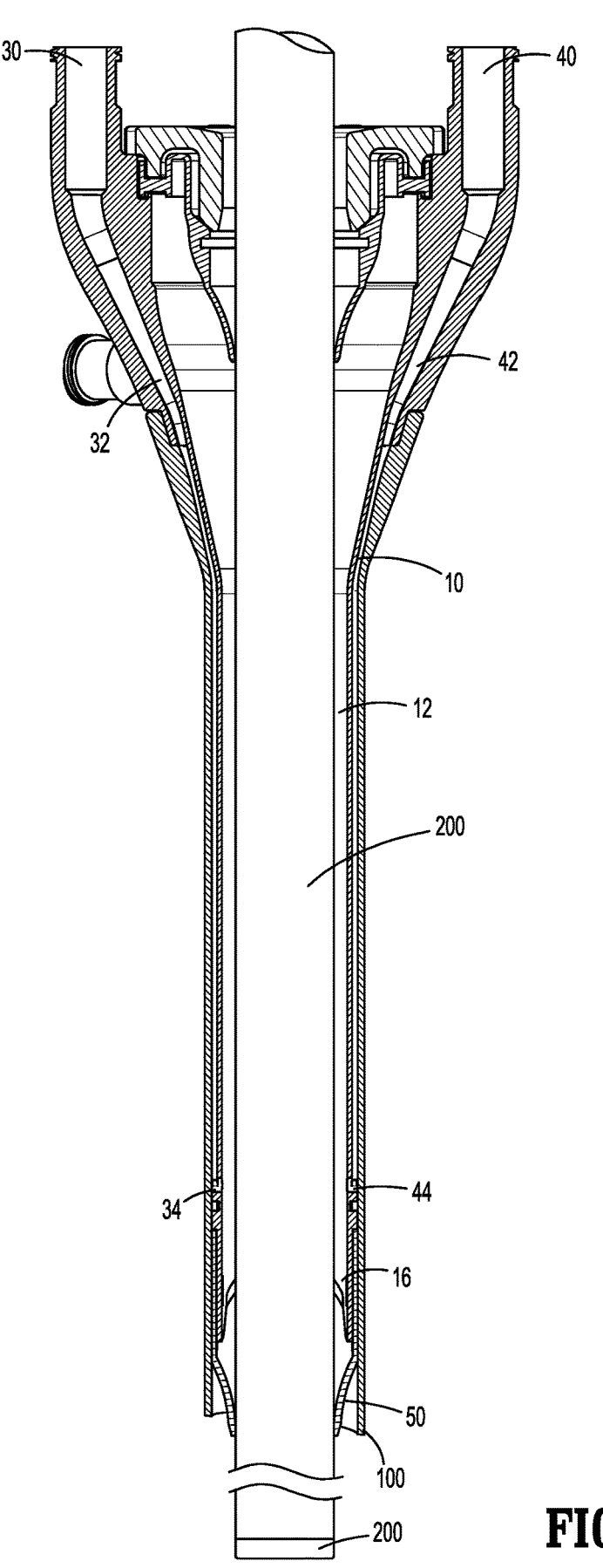
FIG. 5 is a side cross-sectional view of the trocar shown along line 5-5 in FIG. 1.

FIG. 5 shows a laparoscope 200 deployed from the trocar 10 through the cannula 100. The vacuum seal 50 is opens when the laparoscope 200 passes therethrough. As shown in FIG. 5, the inlet port 30 is connected to inlet tube 32, which terminates at entry opening 34 at the distal portion 16 of the trocar 10. The inlet port 30, inlet tube 32 and entry opening 34 permit the introduction of liquids and/or gases into the distal portion 16 of the trocar 10. Similarly, the vacuum port 40 is connected to outlet tube 42, which terminates at exit opening 44 at the distal portion 16 of the trocar. The vacuum port 40, outlet tube 42 and exit opening 44 permit the removal of liquids and/or gases from the distal portion 16 of the trocar 10.

Figure 6:
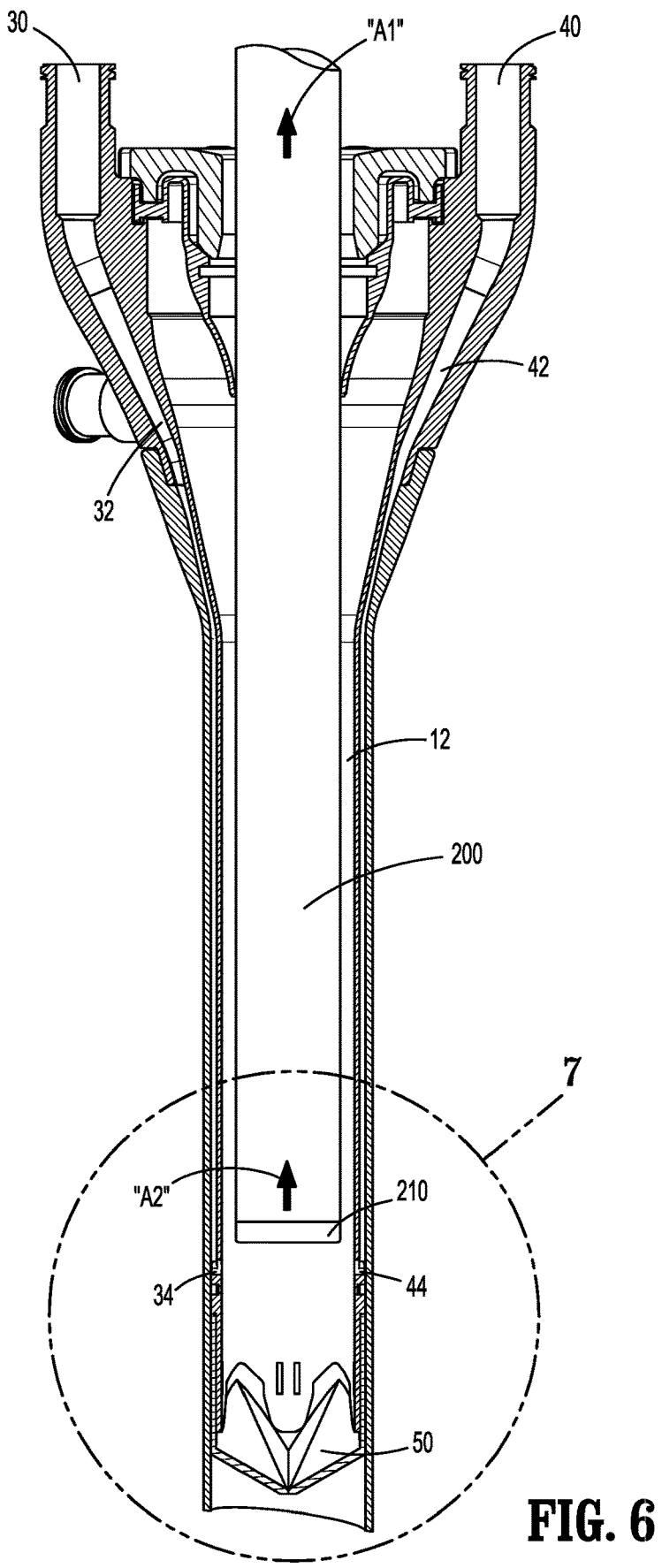
FIG. 6 is a side view of the trocar of FIG. 5, showing movement of a laparoscope within the trocar.
Figure 7:
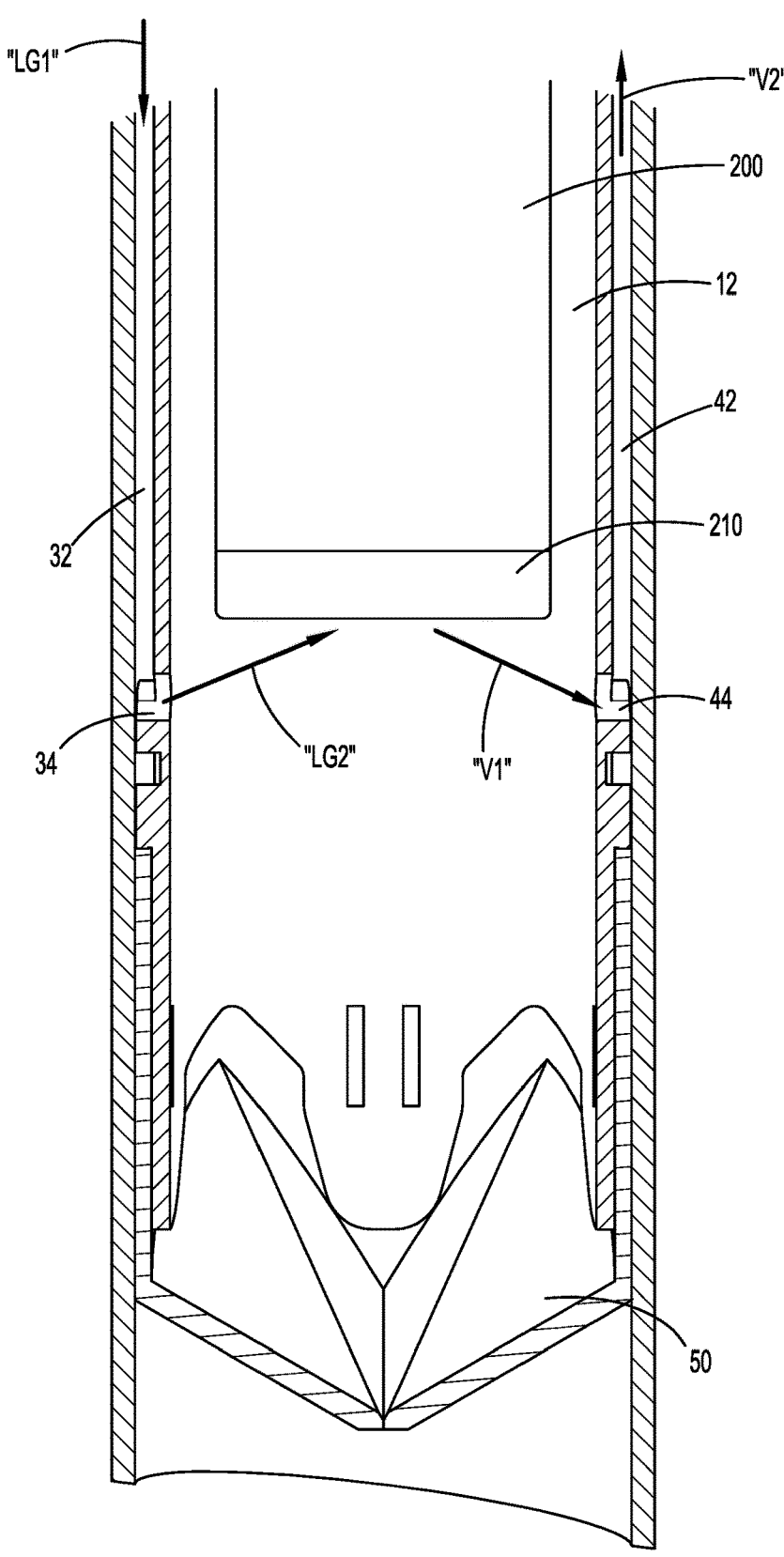
FIG. 7 is an enlarged view of the indicated area of detail shown in FIG. 6.

In use, as shown in greater detail in FIGS. 6-7, the laparoscope 200 in need of cleaning is partially withdrawn proximally within the trocar 10 (indicated by arrows "A1" and "A2" in FIG. 6) so that the lens 210 of the laparoscope 200 is proximal to the vacuum seal 50. A vacuum is drawn by connecting a vacuum source (not shown) to the vacuum port 40. Drawing of the vacuum causes the vacuum seal 50 to form a tight seal.

Liquids and/or gases are then introduced through the inlet port 30. Drawing the vacuum causes the liquids and/or gases to travel through the inlet tube 32, shown as arrow "LG1", and pass through the entry opening 34 into the distal portion 16 of the trocar 10, shown as arrow "LG2", where liquids and/or gases contact the lens 210 of the laparoscope 200, to remove any condensation, tissue, blood, other body fluids, etc. from the lens 210.

Continued drawing of the vacuum causes the liquids, gases, and any other material(s) removed from the laparoscope lens 210 to exit the distal portion 16 of the trocar 10, shown as arrow "V1", by passing through exit opening 44 and through the outlet tube 42, shown as arrow "V2", and out of the trocar 10 through the vacuum port 40.

For example, in aspects, a laparoscope to be cleaned may first be subjected to a liquid, such as water and/or saline, to clean the lens of the laparoscope. After the lens has been cleaned, it may then be dried by introducing air, carbon dioxide, or the like, in the same manner as the liquid was introduced to quickly dry the lens.

In aspects, the liquid used to clean the end of the medical device, such as the lens of a laparoscope, may be water combined with saline, in aspects about 0.9% saline. To minimize fogging issues, the liquid can be at a temperature of about 37° C. The temperature of the gas used for drying, such as carbon dioxide, can also be at 37° C. to prevent lens fogging.

The cleaning cycle can be manually operated, or automated. For example, for an automated system, starting the vacuum will start the automatic cycle, where the vacuum is drawn, fluids introduced and removed, gases introduced and removed, and the cycle is concluded. In general a cleaning cycle will take about 20 seconds.

After cleaning, the lens may then be moved distally (not shown), where it passes through the vacuum seal 50 and back into the patient's body for further use.

The trocar of the disclosure and its associated methods of use have several advantages including, for example:
enhance surgical efficiency, and maintain image quality.
reduce cleaning lens time.
reduce surgical operation and anesthesia time.
avoid the risk of infection.

Any of the components described herein may be fabricated from either metals, plastics, resins, composites or the like taking into consideration strength, durability, wearability, weight, resistance to corrosion, ease of manufacturing, cost of manufacturing, and the like. In aspects, the elongate body of the trocar may be made of metals, such as stainless steel, while the seals may be formed of an elastomeric plastic or rubber.

It will be understood that various modifications may be made to the disclosed trocars. Therefore, the above description should not be construed as limiting, but merely as exemplifications of aspects of the disclosure. Those skilled in the art will envision other modifications within the scope and spirit of the disclosure. For example, any and all features of one described aspect may be suitably incorporated into another aspect.

What is claimed is:

1. A trocar system, comprising:
a cannula having an outer surface and an inner surface, the inner surface defining a first lumen; and
a trocar configured for reception into the first lumen of the cannula, the trocar comprising:
an elongate body having a longitudinal axis extending between a proximal portion and a distal portion, the elongate body comprising an outer surface and an inner surface, the outer surface of the elongate body having at least a first channel and a second channel, the inner surface of the elongate body defining a second lumen configured to receive a laparoscope;
a seal assembly in communication with the second lumen at the proximal portion of the elongate body;
an inlet port at the proximal portion of the elongate body, the inlet port being in communication with a fluid source;
a vacuum port at the proximal portion of the elongate body, the vacuum port being in communication with a vacuum;
an inlet tube being in fluid communication with the inlet port, the inlet tube formed by the first channel of the elongate body and the inner surface of the cannula, the inlet tube having a first portion extending substantially longitudinally with respect to the elongate body and a second portion extending substantially circumferentially with respect to the elongate body, the second portion of the inlet tube terminating at an entry opening configured to deliver a fluid into the second lumen;
an outlet tube being in fluid communication with the vacuum port, the outlet tube formed by the second channel and the inner surface of the cannula, the outlet tube terminating at an exit opening at the distal portion of the elongate body, the outlet tube being configured to enable the fluid to be removed from the second lumen via the exit opening; and a vacuum seal being configured to seal the second lumen at the distal portion of the elongate body, wherein the fluid is drawn from the entry opening across a lens of the laparoscope and out the exit opening by operation of the vacuum.

2. The trocar system of claim 1, wherein the vacuum seal is formed of multiple leaflets.

3. The trocar system of claim 1, wherein the vacuum seal is distal to the entry opening of the inlet tube and the exit opening of the outlet tube.

4. The trocar system of claim 1, wherein the inlet port is positioned on a first side of the seal assembly at the proximal portion of the elongate body.

5. The trocar system of claim 4, wherein the vacuum port is positioned on a second side of the seal assembly at the proximal portion of the elongate body.

6. The trocar system of claim 1, wherein the fluid is a gas delivered into the inlet port and through the inlet tube into the lumen via the entry opening within the distal portion of the elongate body.

7. The trocar system of claim 6, wherein the vacuum seal is configured to prevent the gas from exiting a distal end of the lumen.

8. The trocar system of claim 6, wherein the gas is drawn from the lumen into the exit opening and through the outlet tube by the vacuum connected to the vacuum port at the proximal portion of the elongate body.

9. The trocar system of claim 8, wherein the vacuum seal is maintained in a closed position when the vacuum connected to the vacuum port draws the gas into the exit opening and through the outlet tube.

10. The trocar system of claim 8, wherein the lens of the laparoscope positioned within the lumen proximal to the vacuum seal is cleaned as the gas is drawn across the lens into the exit opening.

11. The trocar system of claim 1, wherein the fluid is a liquid.

12. The trocar system of claim 11, wherein the liquid exits the lumen via the exit opening through the outlet tube and out the vacuum port at the proximal portion of the elongate body.

13. A trocar system, comprising:

a cannula having an outer surface and an inner surface, the inner surface defining a first lumen; and a trocar configured for reception into the first lumen of the cannula, the trocar comprising:

an elongate body having a longitudinal axis extending between a proximal portion and a distal portion, the elongate body comprising an outer surface and an inner surface, the outer surface of the elongate body having at least a first channel and a second channel, the inner surface of the elongate body defining a second lumen configured to receive a laparoscope;

a seal assembly in communication with the second lumen at the proximal portion of the elongate body;

an inlet port at the proximal portion of the elongate body, the inlet port being in communication with a fluid source;

a vacuum port at the proximal portion of the elongate body, the vacuum port being in communication with a vacuum;

an inlet tube being in fluid communication with the inlet port, the inlet tube formed by the first channel of the elongate body and the inner surface of the cannula, the inlet tube having a first portion extending substantially longitudinally with respect to the elongate body and a second portion extending substantially circumferentially with respect to the elongate body, the second portion of the inlet tube terminating at an entry opening configured to deliver a first fluid and a second fluid into the second lumen, wherein the first fluid is different from the second fluid;

an outlet tube being in fluid communication with the vacuum port, the outlet tube formed by the second channel and the inner surface of the cannula, the outlet tube terminating at an exit opening at the distal portion of the elongate body, the outlet tube being configured to enable the first fluid and the second fluid to be removed from the second lumen via the exit opening; and a vacuum seal being configured to seal the second lumen at the distal portion of the elongate body, wherein a lens of the laparoscope positioned within the second lumen between the seal assembly and the vacuum seal is cleaned when the first fluid and the second fluid are drawn from the entry opening across the lens of the laparoscope and out the exit opening by operation of the vacuum.

14. The trocar system of claim 13, wherein the first fluid is a liquid and the second fluid is a gas.

15. The trocar system of claim 13, wherein the first fluid is delivered into and removed from the lumen, and then the second fluid is delivered into and removed from the lumen.

16. The trocar system of claim 13, wherein debris associated with the lens is removed when the first fluid is drawn across the lens by the vacuum, and wherein the lens is dried when the second fluid is drawn across the lens by the vacuum.

17. The trocar system of claim 1, wherein the second portion of the inlet tube tapers to terminate at the entry opening.

18. The trocar system of claim 13, wherein the second portion of the inlet tube tapers to terminate at the entry opening.

* * * * *